(12) United States Patent
Shaltis et al.

(10) Patent No.: US 10,398,448 B2
(45) Date of Patent: Sep. 3, 2019

(54) ARTERIOVENOUS FISTULA MATURATION

(71) Applicant: KPR U.S., LLC, Mansfield, MA (US)

(72) Inventors: Phillip Shaltis, Sharon, MA (US); Gaurav Girdhar, North Attleboro, MA (US); Arnaz Malhi, Watertown, MA (US)

(73) Assignee: KPR U.S., LLC, Mansfield, MA (US)

( * ) Notice: Subject to any disclaimer, the term of this patent is extended or adjusted under 35 U.S.C. 154(b) by 246 days.

(21) Appl. No.: 14/747,134

(22) Filed: Jun. 23, 2015

(65) Prior Publication Data

US 2015/0366565 A1 Dec. 24, 2015

Related U.S. Application Data

(60) Provisional application No. 62/015,752, filed on Jun. 23, 2014.

(51) Int. Cl.
*A61B 17/135* (2006.01)
*A61B 5/00* (2006.01)
(Continued)

(52) U.S. Cl.
CPC ........ *A61B 17/1355* (2013.01); *A61B 5/0295* (2013.01); *A61B 5/02416* (2013.01); *A61B 5/4848* (2013.01); *A61B 5/7292* (2013.01); *A61H 9/0078* (2013.01); *A61B 5/0245* (2013.01); *A61B 5/0402* (2013.01); *A61B 2017/00106* (2013.01); *A61B 2017/00154* (2013.01); *A61B 2090/064* (2016.02); *A61B 2562/0247* (2013.01); *A61H 2201/164* (2013.01); *A61H 2201/1635* (2013.01); *A61H 2201/5058* (2013.01); *A61H 2201/5071* (2013.01); *A61H 2230/065* (2013.01); *A61H 2230/208* (2013.01)

(58) Field of Classification Search
CPC .............. A61B 17/135; A61B 17/1355; A61H 9/0078; A61H 9/0092
See application file for complete search history.

(56) References Cited

U.S. PATENT DOCUMENTS 3,825,008 A * 7/1974 Shook ................. A61B 17/135
128/DIG. 20
4,054,129 A 10/1977 Byars et al.
(Continued)

FOREIGN PATENT DOCUMENTS

EP 2540329 A1 1/2013
EP 2712598 A1 4/2014
(Continued)

OTHER PUBLICATIONS

Rus RR, Ponikvar R, Kenda RB, Buturovic-Ponikvar J., "Effect of intermittent compression of upper arm veins on forearm vessels in patients with end-stage renal disease". Hemodial Int. Jul. 2005; 9(3):275-80.
(Continued)

*Primary Examiner* — Alexander J Orkin
(74) *Attorney, Agent, or Firm* — Jacob Lenzke

(57) ABSTRACT

A compression device controller controls operation of a compression device to inflate at least one inflatable bladder to control forces applied to an arteriovenous fistula of a subject for maturing the arteriovenous fistula.

16 Claims, 8 Drawing Sheets

(51) Int. Cl.
*A61B 5/024* (2006.01)
*A61B 5/0295* (2006.01)
*A61H 9/00* (2006.01)
A61B 17/00 (2006.01)
A61B 5/0245 (2006.01)
A61B 5/0402 (2006.01)
A61B 90/00 (2016.01)

(56) References Cited

U.S. PATENT DOCUMENTS

| | | | |
|---|---|---|---|
| 4,206,751 | A | 6/1980 | Schneider |
| 4,418,690 | A | 12/1983 | Mummert |
| 4,548,198 | A | 10/1985 | Manes |
| 4,715,849 | A | 12/1987 | Gion et al. |
| 4,781,189 | A * | 11/1988 | Vijil-Rosales ....... A61B 17/135 |
| | | | 128/DIG. 20 |
| 6,231,532 | B1 | 5/2001 | Watson et al. |
| 6,463,934 | B1 | 10/2002 | Johnson et al. |
| 7,118,534 | B2 | 10/2006 | Ward et al. |
| 8,070,707 | B2 | 12/2011 | Gelfand et al. |
| 8,157,754 | B2 | 4/2012 | Weintraub et al. |
| 2003/0236548 | A1 | 12/2003 | Hovanes et al. |
| 2005/0075597 | A1* | 4/2005 | Vournakis ............... A61L 15/44 |
| | | | 604/4.01 |
| 2006/0200195 | A1* | 9/2006 | Yang .................. A61B 5/02405 |
| | | | 606/202 |
| 2007/0032818 | A1 | 2/2007 | McEwen et al. |
| 2008/0033307 | A1* | 2/2008 | Baudoin ............ A61B 5/02225 |
| | | | 600/490 |
| 2008/0103397 | A1 | 5/2008 | Barak |
| 2009/0124912 | A1 | 5/2009 | McEwen et al. |
| 2009/0234262 | A1* | 9/2009 | Reid, Jr. ................ A61B 5/026 |
| | | | 601/152 |
| 2011/0190807 | A1 | 8/2011 | Redington et al. |
| 2011/0251635 | A1 | 10/2011 | Caldarone |
| 2012/0065482 | A1 | 3/2012 | Robinson et al. |
| 2014/0066786 | A1* | 3/2014 | Naghavi ............ A61B 17/1355 |
| | | | 600/481 |

FOREIGN PATENT DOCUMENTS

| | | |
|---|---|---|
| GB | 2085198 A | 4/1982 |
| SU | 1119681 A | 10/1984 |
| WO | 98/51366 A1 | 11/1998 |
| WO | 2006116837 A1 | 11/2006 |

OTHER PUBLICATIONS

Rus R, Ponikvar R, Kenda RB, Buturovic-Ponikvar J., "Effect of handgrip training and intermittent compression of upper arm veins on forearm vessels in patients with end-stage renal failure". Ther Apher Dial. Jun. 2005; 9(3):241-4.

Himburg HA, Dowd SE, Friedman MH, "Frequency-dependent response of the vascular endothelium to pulsatile shear stress". Am J Physiol Heart Ciro Physiol. Jul. 2007; 293(1):H645-53. Epub Feb. 23, 2007.

Dai G, Kaazempur-Mofrad MR, Natarajan S, Zhang Y, Vaughn S, Blackman BR, Kamm RD, Garcia-Cardena G, Gimbrone MA Jr., "Distinct endothelial phenotypes evoked by arterial waveforms derived from atherosclerosis-susceptible and -resistant regions of human vasculature". Proc Natl Acad Sci U S A. Oct. 12, 2004; 101(41):14871-6.

Japerse, JL, Seals DR, and Callister R, "Active forearm blood flow adjustments to handgrip exercise in young and older healthy men". J. of Physiology, Jan. 15, 1994, 474(2):353-360.

Pyke, K.E. and Tschakovsky, M.E., "The relationship between shear stress and flow-mediated dilatation: implications for the assessment of endothelial function," J. Physiol 568.2 (2005) pp. 357-369.

International Search Report and Written Opinion for Application No. PCT/US2015/037110, dated Aug. 17, 2015, 11 pages.

* cited by examiner

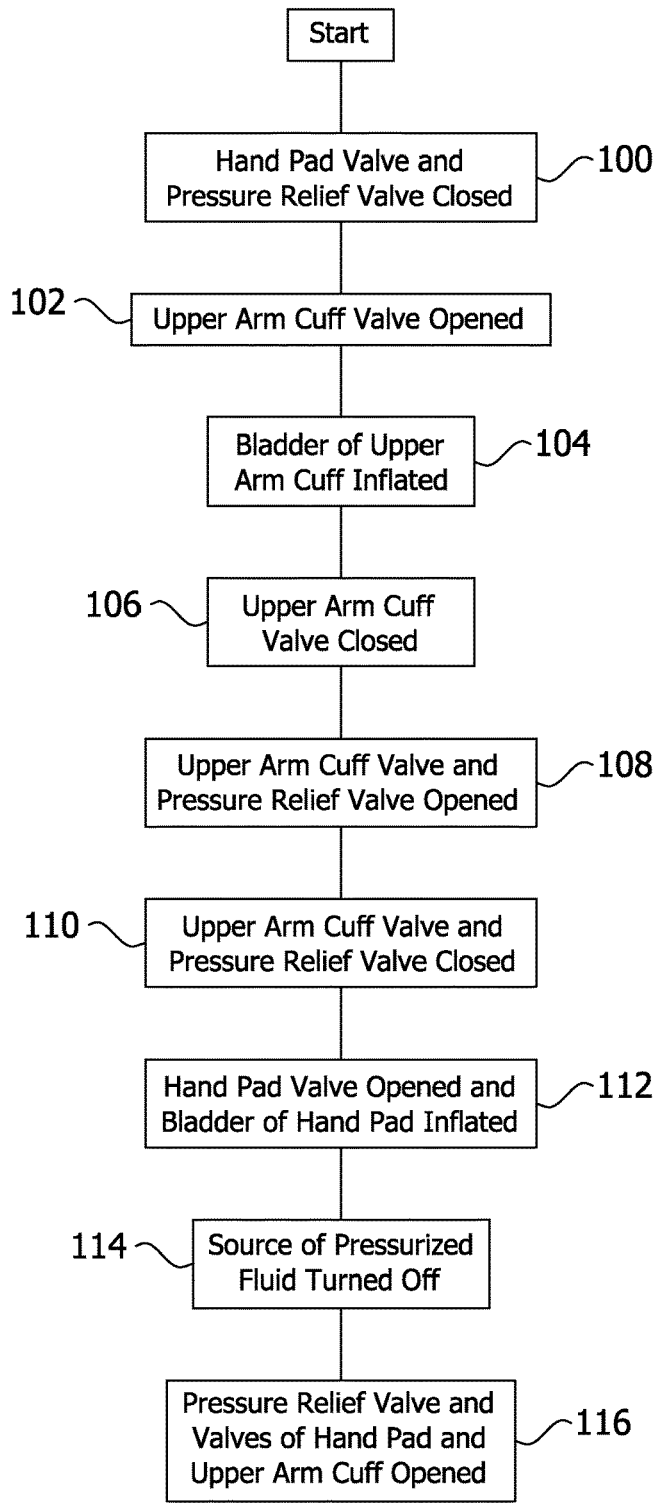

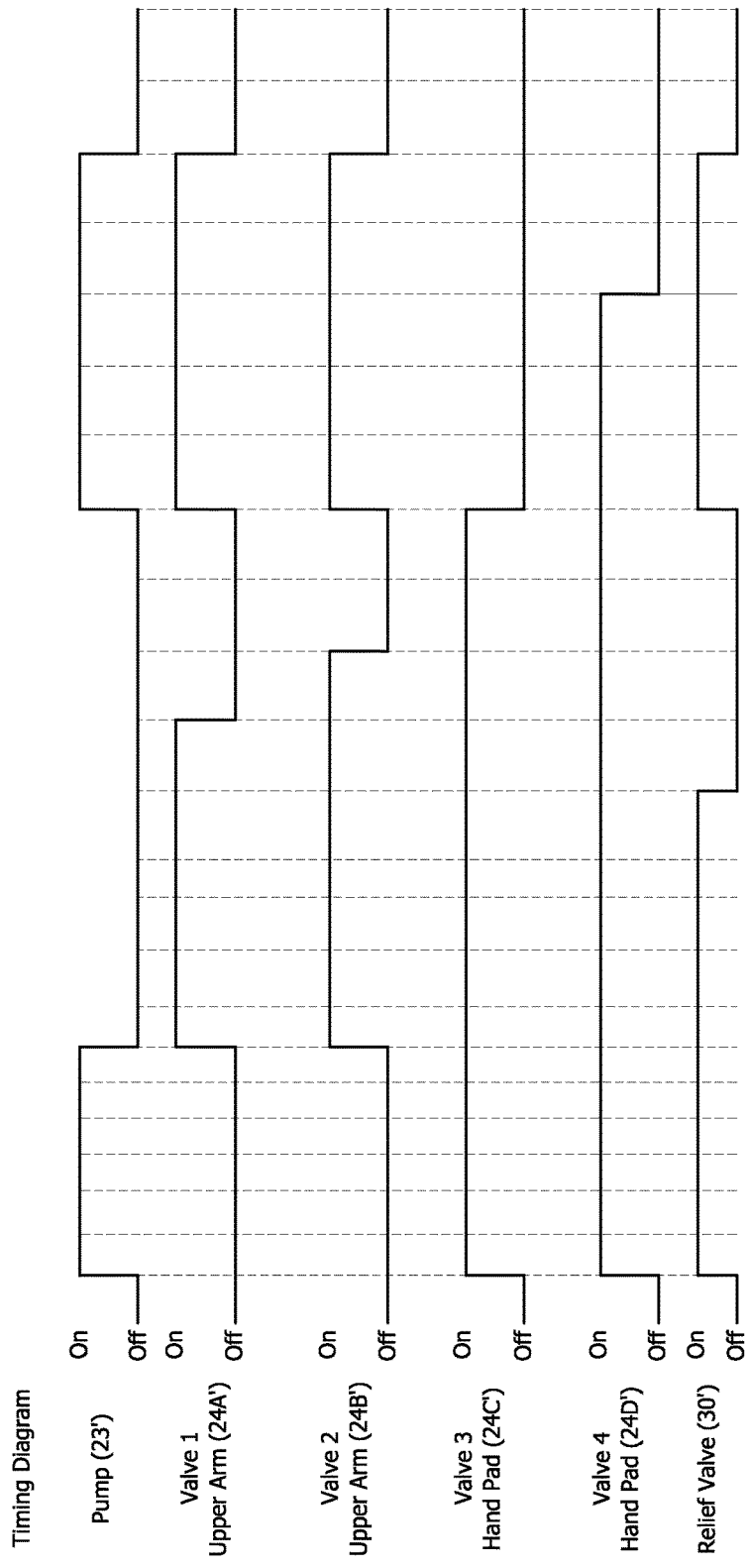

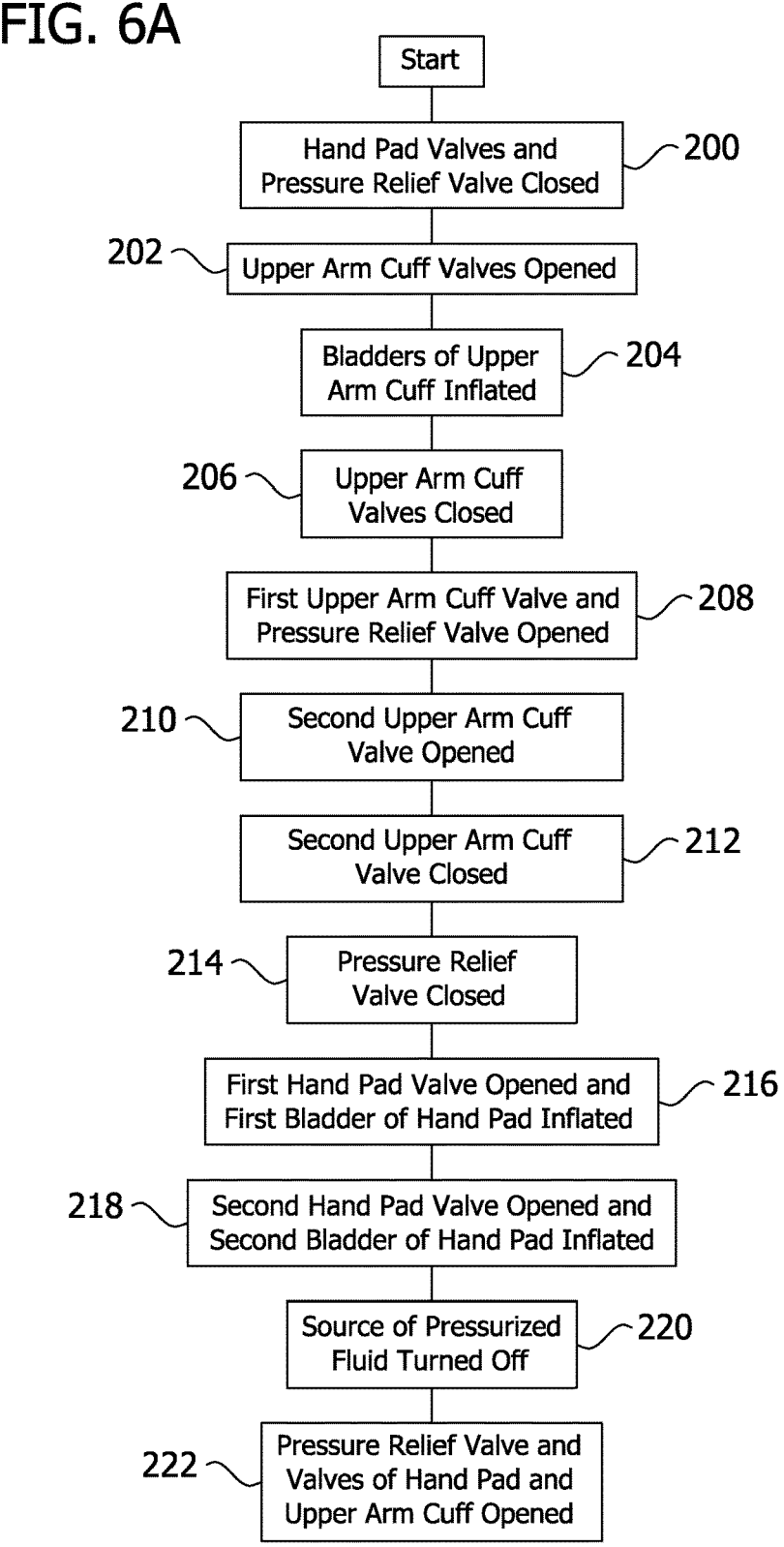

ARTERIOVENOUS FISTULA MATURATION

CROSS-REFERENCE TO RELATED APPLICATION

The present application claims the benefit of, and priority to, U.S. Provisional Application Ser. No. 62/015,752 filed Jun. 23, 2014, the entirety of which is incorporated herein by reference.

BACKGROUND

Treatment of patients with end stage renal disease requires creation and maintenance of adequate vascular access. One type of vascular access is an arteriovenous (AV) fistula for, for example, the administration of hemodialysis to a patient. An AV fistula can be surgically created by connecting a patient's vein to the patient's artery, bypassing capillaries in that area of the patient's body. AV fistulas have low complication rates and are, thus, a commonly used method of achieving vascular access.

The surgically created AV fistula must mature to become suitable for repeated access, as may be required for hemodialysis. Maturation is the process by which the AV fistula, and in particular the vein forming the fistula, receives blood flow to increase the vein's diameter and visibility. Maturation of AV fistulas, however, can take 4-6 weeks (and even longer in pediatric patients). Moreover, a significant number of fistulas fail to mature (e.g., fail to reach target access flow and venous diameter) at the end of this maturation period.

SUMMARY

A compression device controller controls operation of a compression device to inflate at least one inflatable bladder to control forces applied to an AV fistula of a subject. As compared to the absence of applied forces and/or to the application of uncontrolled forces (e.g., such as through squeezing a ball), the controlled forces applied to the AV fistula improve maturation of the AV fistula.

In one aspect, a method includes directing pressurized fluid to inflate at least one inflatable bladder of one or more compression garments secured to an outer portion of a limb of a subject. Forces applied to an arteriovenous fistula in the limb of the subject are controlled based at least in part on the directed inflation of the at least one inflatable bladder.

In some embodiments, blood flow through the fistula is affected to stimulate cellular activity to increase the internal and external diameters of the arteriovenous fistula.

In certain embodiments, a computer executing instructions embodied on a nontransitory computer readable storage medium of the computer carries out the steps of directing pressurized fluid and controlling forces.

In some embodiments, physiological parameter signals representative of one or more physiological parameters of the subject are received in the computer and the computer executable instructions are executed at least in part based on the physiological parameter signals.

In certain embodiments, the physiological parameter signals are signals indicative of natural pulsatile flow through the arteriovenous fistula. Inflation of the at least one inflatable bladder alters the physiological parameter signal from a natural pulsatile flow signal to a modified flow signal.

In some embodiments, a pressure signal is received from a pressure sensor in fluid communication with the at least one inflatable bladder. The pressure signal is indicative of pressure in the at least one inflatable bladder. Inflation of at least one inflatable bladder is based at least in part on the received pressure signal.

In certain embodiments, a signal is received indicative of natural pulsatile blood flow through the arteriovenous fistula. The at least one inflatable bladder is cyclically inflated and deflated, with initiation each inflation sequence of the at least one inflatable bladder is based at least in part on the signal indicative of blood flow through the arteriovenous fistula.

In some embodiments, the at least one inflatable bladder is inflated to alter the signal from a natural pulsatile flow signal to a modified flow signal.

In certain embodiments, a waveform of blood flow through the arteriovenous fistula based at least in part upon the signal indicative of natural pulsatile blood flow through the arteriovenous fistula is determined. The at least one inflatable bladder is inflated based at least in part on the determined waveform.

In some embodiments, the at least one inflatable bladder is inflated in a predetermined pattern relative to the waveform.

In certain embodiments, the at least one inflatable bladder is inflated to augment the determined waveform from a natural pulsatile waveform to a modified non-pulsatile waveform.

In some embodiments, the received signal indicative of natural pulsatile blood flow through the arteriovenous fistula is at least one of a measure of blood pulsation of the subject received from a pulse oximeter arranged at the at least one inflatable bladder, a measure of electrical activity of the subject's heart received from an electrocardiogram connected to the subject, and a measure of pressure received from the pressure sensor in fluid communication with the at least one inflatable bladder.

In certain embodiments, the one or more compression garments include a compression garment distal to the arteriovenous fistula and directing pressurized fluid to inflate the at least one inflatable bladder includes inflating the at least one inflatable bladder to compress an outer portion of the limb distal to the arteriovenous fistula.

In some embodiments, a first inflatable bladder disposed on the limb proximal to the arteriovenous fistula is inflated to compress an outer portion of the limb proximal to the arteriovenous fistula, and a second inflatable bladder disposed on the limb distal to the arteriovenous fistula is inflated to compress an outer portion of the limb distal to the arteriovenous fistula a period of time after the first inflatable bladder is inflated.

In certain embodiments, the second inflatable bladder is inflated after the first inflatable bladder has been deflated.

In some embodiments, a plurality of inflatable bladders of the compression garment are inflated in sequence from a proximal-most inflatable bladder to a distal-most inflatable bladder.

In certain embodiments, a therapeutic effect is imparted on the arteriovenous fistula.

In some embodiments, thrombogenic material is removed from the arteriovenous fistula.

In certain embodiments, a bladder distal to the arteriovenous fistula is inflated to remove the thrombogenic material.

In some embodiments, the at least one inflatable bladder is inflated to change blood flow through the arteriovenous fistula to remove thrombogenic material from the arteriovenous fistula.

In certain embodiments, a sensor signal is received indicative of thrombogenic material in the vicinity of the arteriovenous fistula. The at least one inflatable bladder is inflated based at least in part on the received sensor signal indicative of thrombogenic material.

In some embodiments, the received sensor signal is an ultrasound sensor signal.

In another aspect, a compression device controller includes one or more processors and computer executable instructions embodied on a nontransitory computer readable storage medium. The computer executable instructions include instructions, that when executed, cause the one or more processors to direct pressurized fluid to inflate at least one inflatable bladder of one or more compression garments secured to an outer portion of a limb of a subject. Forces applied to an arteriovenous fistula in the limb of the subject are controlled based at least in part on the directed inflation of the at least one inflatable bladder.

In certain embodiments, the computer readable storage medium further includes instructions for causing the one or more processors to receive a pressure signal from a pressure sensor in fluid communication with the at least one inflatable bladder. The pressure signal is indicative of pressure in the at least one inflatable bladder. Inflation of the at least one inflatable bladder is based at least in part on the received pressure signal.

In some embodiments, the computer readable storage medium further includes instructions for causing the one or more processors to receive a signal indicative of natural pulsatile blood flow through the arteriovenous fistula. The at least one inflatable bladder is cyclically inflated and deflated, with initiation each inflation sequence of the at least one inflatable bladder based at least in part on the signal indicative of the natural pulsatile blood flow through the arteriovenous fistula.

In certain embodiments, the at least one inflatable bladder is inflated to alter the signal from a natural pulsatile flow signal to a modified flow signal.

In some embodiments, the computer readable storage medium further includes instructions for causing the one or more processors to determine a waveform of blood flow through the arteriovenous fistula based at least in part upon the signal indicative of natural pulsatile blood flow through the arteriovenous fistula. The one or more processors inflate the at least one inflatable bladder based at least in part on the determined waveform.

In certain embodiments, the at least one inflatable bladder is inflated in a predetermined pattern relative to the waveform.

In some embodiments, the at least one inflatable bladder is inflated to augment the determined waveform from a natural pulsatile waveform to a modified non-pulsatile waveform.

In certain embodiments, the one or more processors receive at least one of a measure of blood pulsation of the subject from a pulse oximeter arranged at the at least one inflatable bladder, a measure of electrical activity of the subject's heart from an electrocardiogram connected to the subject, and a measure of pressure from the pressure sensor in fluid communication with the at least one inflatable bladder.

In some embodiments, the one or more processors inflate the at least one inflatable bladder to compress an outer portion of the limb distal to the arteriovenous fistula.

In certain embodiments, the one or more processors inflate a first inflatable bladder identified by the one or more processors as being disposed proximal to the arteriovenous fistula to compress an outer portion of the limb proximal to the arteriovenous fistula, and inflate a second inflatable bladder identified by the one or more processors as being disposed distal to the arteriovenous fistula to compress an outer portion of the limb distal to the arteriovenous fistula a period of time after the first inflatable bladder is inflated.

In some embodiments, the second inflatable bladder is inflated after the first inflatable bladder has been deflated.

In certain embodiments, the one or more processors inflate a plurality of inflatable bladders of the compression garment in sequence from a proximal-most inflatable bladder to a distal-most inflatable bladder.

In some embodiments, the one or more processors change blood flow through the arteriovenous fistula in the limb of the subject to impart a therapeutic effect on the arteriovenous fistula.

In certain embodiments, the one or more processors change blood flow through the arteriovenous fistula to remove thrombogenic material from the arteriovenous fistula.

In some embodiments, a sensor signal indicative of thrombogenic material at the arteriovenous fistula is received. The at least one inflatable bladder is inflated to remove the thrombogenic material from the arteriovenous fistula.

In certain embodiments, the one or more processors inflate a bladder distal to the arteriovenous fistula.

In some embodiments, the one or more processors receive a sensor signal indicative of thrombogenic material in the vicinity of the arteriovenous fistula. The one or more processors inflate the at least one inflatable bladder based at least in part on the received sensor signal indicative of thrombogenic material.

In certain embodiments, the received sensor signal is an ultrasound sensor signal.

In another aspect, a system includes at least one compression garment securable to an outer portion of a limb of a subject. The at least one compression garment includes at least one inflatable bladder and a supply of pressurized fluid. At least one valve is adjustable to control fluid communication between the supply of pressurized fluid and the at least one inflatable bladder. A compression device controller is in electrical communication with the supply of pressurized fluid and the at least one valve. The controller operates the at least one inflatable bladder to control forces applied to an arteriovenous fistula of a subject for maturing the arteriovenous fistula Embodiments can include one or more of the following advantages.

In some embodiments, a length of time for a subject's AV fistula to mature is shortened by controlling forces applied to the AV fistula using an inflatable bladder.

In certain embodiments, the likelihood that a subject's AV fistula will fully mature is increased by controlling forces applied to the AV fistula using an inflatable bladder.

In some embodiments, maturation of a subject's AV fistula is facilitated without requiring active muscle contraction by the subject. For example, maturation is achieved without the subject having to clench his or her fist to generate blood flow in the fistula. This can be useful, for example, to expand the availability of treatment to patients with compromised strength.

In some embodiments, forces applied to an AV fistula in a limb of a subject are controlled to provide a steady flow of blood through the fistula. It is believed that the steady flow of blood prevents stenosis from occurring in the fistula.

BRIEF DESCRIPTION OF THE DRAWINGS

FIG. 3A is a flow chart of an operating procedure for the compression system of FIG. 1.

FIG. 6 is a timing diagram for inflation and deflation of the garments of the compression system of FIG. 4

FIG. 6A is a flow chart of an operating procedure for the compression system of FIG. 4.

DETAILED DESCRIPTION

Compression systems and methods of the present disclosure enhance blood flow through an AV fistula in a subject to increase the likelihood of an acceptable maturation outcome of the AV fistula and, additionally or alternatively, to decrease the time between the creation of the AV fistula and the initial cannulation of the AV fistula.

Figure 1:
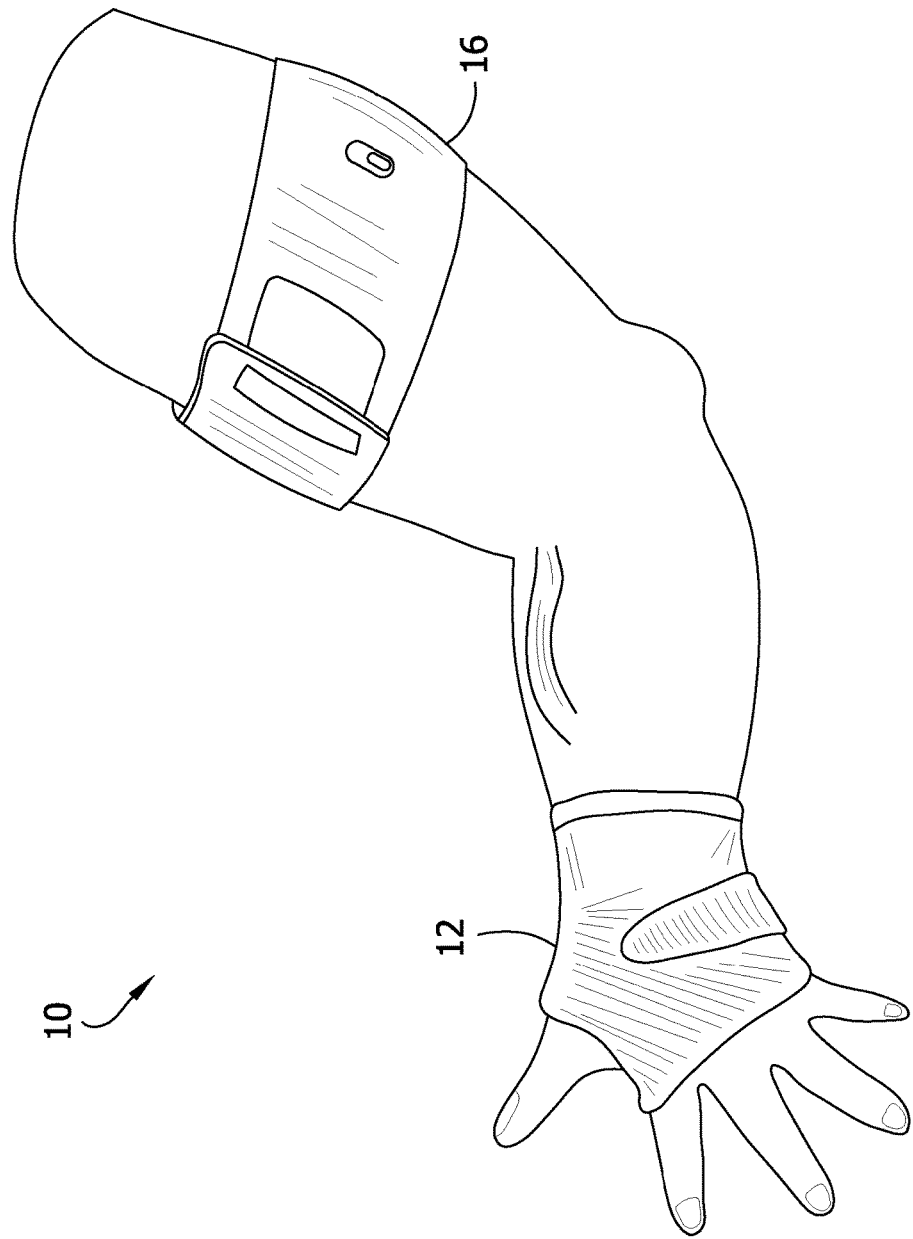
FIG. 1 is a schematic representation of a compression system including multiple garments, shown secured to a limb of a subject for enhancing AV fistula maturation.
Figure 2:
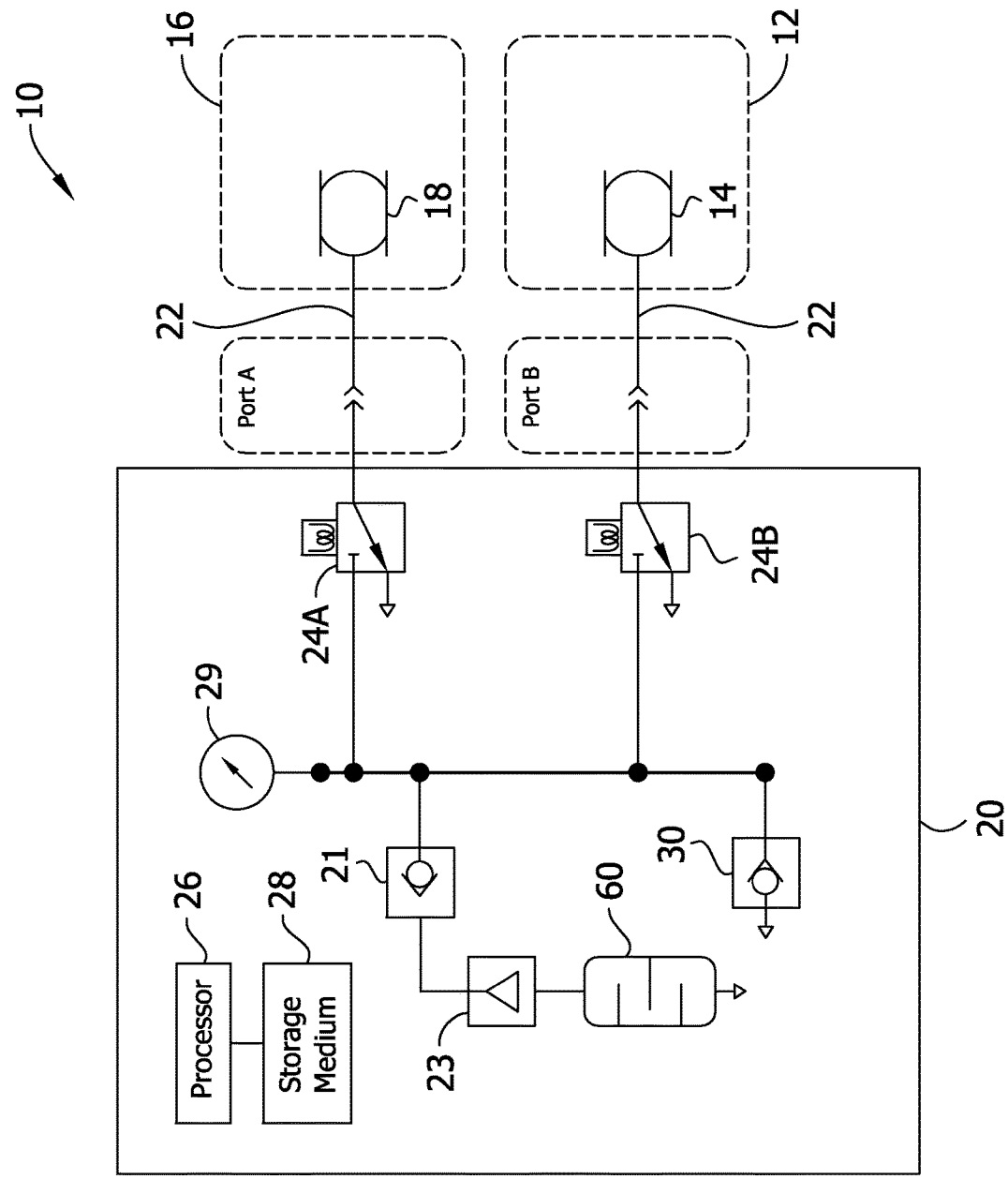
FIG. 2 is a diagram of a pneumatic circuit of the compression system of FIG. 1.

Referring now to FIGS. 1 and 2, a compression system 10 includes a controller 20 in fluid communication with a first compression garment 12 and a second compression garment 14 via respective tubing sets 22 through ports A and B, respectively. The first compression garment 12 includes at least one inflatable bladder 14, and the second compression garment 16 includes at least one inflatable bladder 18.

In certain embodiments, the first compression garment 12 is a hand pad, including a single inflatable bladder 14, the hand pad securable to the subject's hand. In some embodiments, the second compression garment 16 is an arm cuff, including a single inflatable bladder 18, the arm cuff securable over a portion of the subject's upper arm.

As described in further detail below, the controller 20 includes a source of pressurized fluid 23 (e.g., a variable speed pump for pumping air or another fluid), a check valve 21, one or more valves 24, one or more processors 26 in electrical communication with the source of pressurized fluid 23 and the one or more valves 24, a computer-readable storage medium 28, and computer executable instructions embodied on the computer readable storage medium 28 for causing the one or more processors 26 to control the flow of pressurized fluid to the inflatable bladder 14 in the first compression garment 12 and/or the inflatable bladder 18 of the second compression garment 16.

The one or more processors 26 direct fluid from the source of pressurized fluid 23 to inflate the inflatable bladder 14 of the hand pad 12 and/or the inflatable bladder 18 of the arm cuff 16. For example, the one or more processors 26 can actuate the one or more valves 24 to control fluid communication between the source of pressurized fluid and the inflatable bladders 14, 18. Additionally or alternatively, in embodiments in which the source of pressurized fluid 23 is a variable speed pump, the one or more processors 26 can control fluid communication between the source of pressurized fluid and the inflatable bladders 14, 18 by controlling the speed of the variable speed pump.

The one or more valves 24 can be, for example, one valve per inflatable bladder 14, 18 (e.g., 2 to 6 valves 24). Additionally or alternatively, the one or more valves 24 can be electrically actuated, normally closed valves. In general, the one or more valves 24 are disposed between the source of pressurized fluid 23 and the first compression garment 12 and the second compression garment 16. It should be appreciated that the type and number of valves can vary without departing from the scope of the present disclosure.

The compression system 10 can further include a pressure transducer 29 disposed between the source of pressurized fluid 23 and the one or more valves 24 to measure inflation pressure of the inflatable bladders 14, 18. The pressure transducer 29 can be in electrical communication with the one or more processors 26 to facilitate directing fluid from the source of pressurized fluid 23 to inflate the inflatable bladders 14, 18 of the hand pad 12 and arm cuff 16.

In use, as will be explained in greater detail below, the one or more processors 26 direct inflation of the inflatable bladders 14, 18 to apply pressure to the first compression garment 12 and second compression garment 16 to control forces on a surgically created AV fistula in the subject's arm (e.g., in the subject's forearm). For example, the one or more processors 26 can direct pressurized fluid from the source of pressurized fluid 23 to the inflatable bladder 18 of the second compression garment 16 to apply pressure to the subject's upper arm, expanding the diameter of the AV fistula, and then directing pressurized fluid from the source of pressurized fluid 23 to the inflatable bladder 14 of the first compression garment 12 to apply pressure to the subject's hand to push rapidly the increased volume of fluid through the enlarged AV fistula.

In some embodiments, the first compression garment 12 includes a single inflatable bladder 14, and the second compression garment 16 includes a single inflatable bladder 18. In these embodiments, the one or more processors 26 inflate the single inflatable bladder 14 of the first compression garment 12 and the single inflatable bladder 18 of the second compression garment 16. A first valve 24A controls the flow of pressurized fluid from the source of pressurized fluid 23 to the inflatable bladder 18 of the second compression garment 16, and a second valve 24B controls the flow of pressurized fluid from the source of pressurized fluid 23 to the inflatable bladder 14 of the first compression garment 12.

Figure 3:
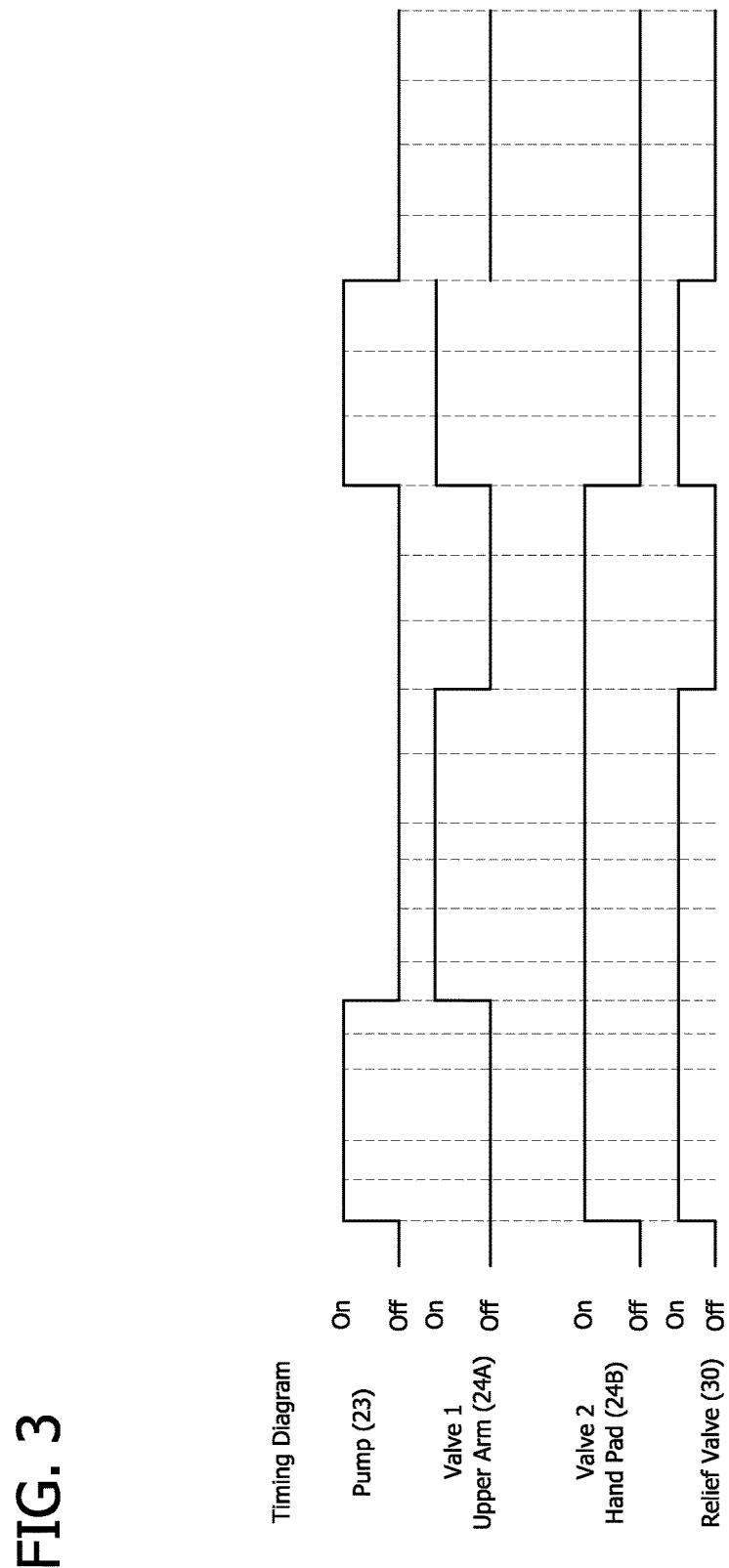
FIG. 3 is a timing diagram for inflation and deflation of the garments of the compression system of FIG. 1.
Figure 4:
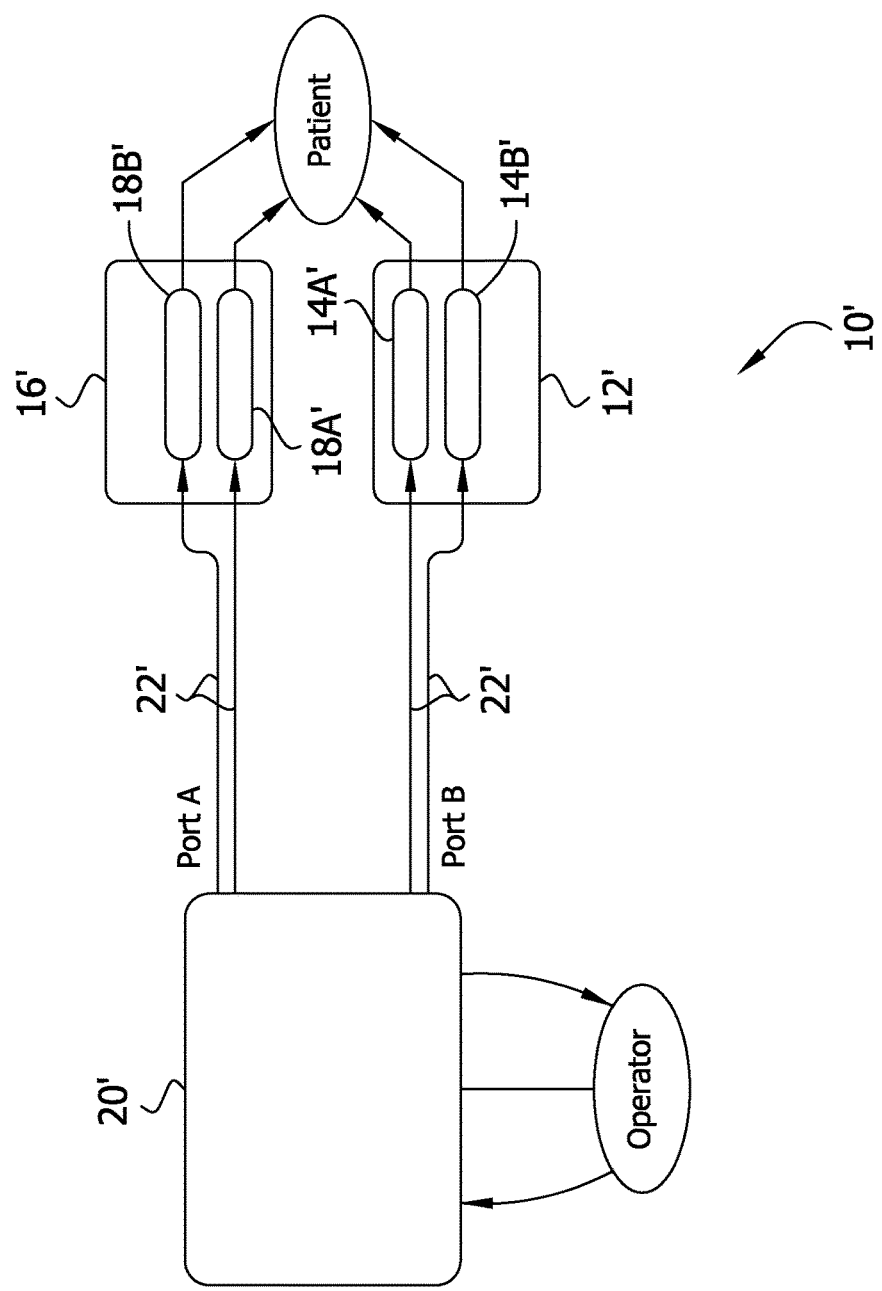
FIG. 4 is a schematic representation of another compression system for enhancing AV fistula maturation.

Referring to FIGS. 2-3A, an exemplary computer-implemented method of operation of the compression system 10 is described. As described in further detail below, the method includes directing pressurized fluid to inflate the inflatable bladders 14, 18 of the first and second compression garments 12, 16, respectively, while the first and second compression garments 12, 16 are secured to an outer portion of a limb of a subject. As also further described in further detail below, the method further includes, based at least in part on the directed inflation of inflatable bladders 14, 18, controlling forces applied (e.g., through the flow of blood) to an AV fistula in the limb of the subject.

The second valve 24B, and a pressure relief valve 30 are closed 100, preventing inflation of the inflatable bladder 14 of the first compression garment 12.

The first valve 24A is open 102 such that the source of pressurized fluid 23 is in fluid communication with the inflatable bladder 18 of the second compression garment 16.

The inflatable bladder 18 of the second compression garment 16 is rapidly inflated 104 (e.g., a rate of about 5 lpm) until the inflatable bladder 18 of the second compression garment 16 reaches a pressure (e.g., a pre-set pressure) sufficient (e.g., about 80 mmHg) to collapse upper arm veins of the subject proximal to the AV fistula.

The first valve 24A is closed 106 and the source of pressurized fluid 23 can be turned off. Closure 106 of the first valve 24A holds the pressure in the inflatable bladder 18. This increased pressure in the inflatable bladder 18 of the second compression garment 16 allows the AV fistula to fill with blood and to dilate due to the capacitive nature of veins. The veins can be allowed to fill for a predetermined period of time. In certain embodiments, the predetermined period of time is about 5 seconds to about 30 seconds (e.g., about 8 seconds to about 10 seconds).

The first valve 24A and the pressure relief valve 30 are opened 108 to allow the inflatable bladder 18 of the second inflation garment 16 to vent quickly. In certain embodiments, the inflatable bladder 18 vents for about one second.

With the inflatable bladder 18 of the second inflation garment 16 at a pressure below 15 mmHg, the first valve 24A and the pressure relief valve 30 are closed 110.

The inflatable bladder 14 of the first compression garment 12 is rapidly pressurized by opening 112 the second valve 24B and running the source of pressurized fluid 23 for a preset amount of time (e.g., 3 seconds) until a pressure greater than the internal pressure of the AV fistula is achieved (e.g., about 100 mmHg). The first valve 24A is closed to restrict pressurization of the first inflatable garment 16.

The source of pressurized fluid 23 can be shut off 114, and the pressure relief valve 30, the first valve 24A, and second valve 24B are opened 116 to facilitate release of the remaining air in the compression system 10.

The timing of the next inflation sequence can occur after a preset rest period. For example, the preset rest period can be between about 30 seconds to about 5 minutes (e.g., about 1 minute).

FIG. 3 illustrates a timing diagram for the inflation and deflation of the inflatable bladders 14, 18. In this embodiment, the valves 24A, 24B and pressure relief valve 30 are normally open valves. Therefore, in the diagram, the indication that the valves are open is indicated by the "off" position of the representative line. It should be appreciated, however, that the valves 24A, 24B could be any combination of normally open or normally closed valves without departing from the present disclosure.

In certain embodiments, the pressure in the inflatable bladder 14 of the first compression garment 12 is cycled while the increased pressure is held in the inflatable bladder 18 of the second compression garment 16. For example, after the arm cuff 16 is inflated, the first valve 24A can be held closed so that the pressure in the first compression garment 12 is held for a predetermined amount of time (e.g., about 4 seconds to about 30 seconds). During that predetermined amount of time, the second valve 24B can be opened and the inflatable bladder 14 of the first compression garment 12 can be inflated so that the pressure in the first compression garment 12 can be increased to a maximum pressure (e.g., about 50 mmHg to about 80 mmHg) in a predetermined amount of time (e.g., about 5 seconds) and allowed to deflate for a period of time (e.g., about 5 seconds) while the pressure in the second compression garment 16 is maintained.

While the first compression garment 12 and the second compression garment 16 have each been described as having a single inflatable bladder 14, 18, it should be appreciated that either or both of the compression garments 12, 16 can include multiple inflatable bladders. The use of multiple inflatable bladders in the compression garments can, for example, increase the amount of the control over the flow of blood within the AV fistula.

Referring now to FIGS. 4-6A, a compression system 10' includes multiple inflatable bladders 14A', 14B', 18A', 18B' in respective first and second compression garments 12', 16'. The system 10' is similar to the system 10 (FIG. 2) incorporating the single bladder system described above, but includes additional valves and ports to control the path of air flow to the additional bladders as described below. For the sake of clarity of explanation and unless otherwise indicated, elements in FIGS. 4 and 5 including primed (') reference numerals are similar to corresponding unprimed reference numerals in FIGS. 1 and 2, to the extent such corresponding primed and unprimed reference numerals are present in both sets of figures. For example, unless otherwise indicated, the one or more processors 26 in FIG. 2 are analogous to the one or more processors 26' in FIG. 5.

Referring now to FIGS. 4-6A, the compression system 10' includes the first compression garment 12' and the second compression garment 16'. The first compression garment 12' includes a first inflatable bladder 14A' and a second inflatable bladder 14B', and the second compression garment 16' includes a first inflatable bladder 18A' and a second inflatable bladder 18B'. The first compression garment 12' can be, for example, a hand pad such that the first inflatable bladder 14A' positionable over a palm of a subject's hand, and the second inflatable bladder 14B' is positionable over the subject's wrist when the first compression garment 12' is worn by the subject. The second compression garment 16' can be, for example, an arm cuff such that the first inflatable bladder 18A' of the second compression garment 16' is positionable over a first portion of the subject's upper arm, and the second inflatable bladder 18B' is positionable over a second portion of the subject's upper arm when the second compression garment 16' is worn by the subject.

The compression system 10' can further include a first valve 24A and a second valve 24B to control the flow of pressurized fluid to the inflatable bladders 18A', 18B' of the second compression garment 16' and a third valve 24C and a fourth valve 24D to control the flow of pressurized fluid to the inflatable bladders 14A', 14B' of the first compression garment 12'.

Figure 5:
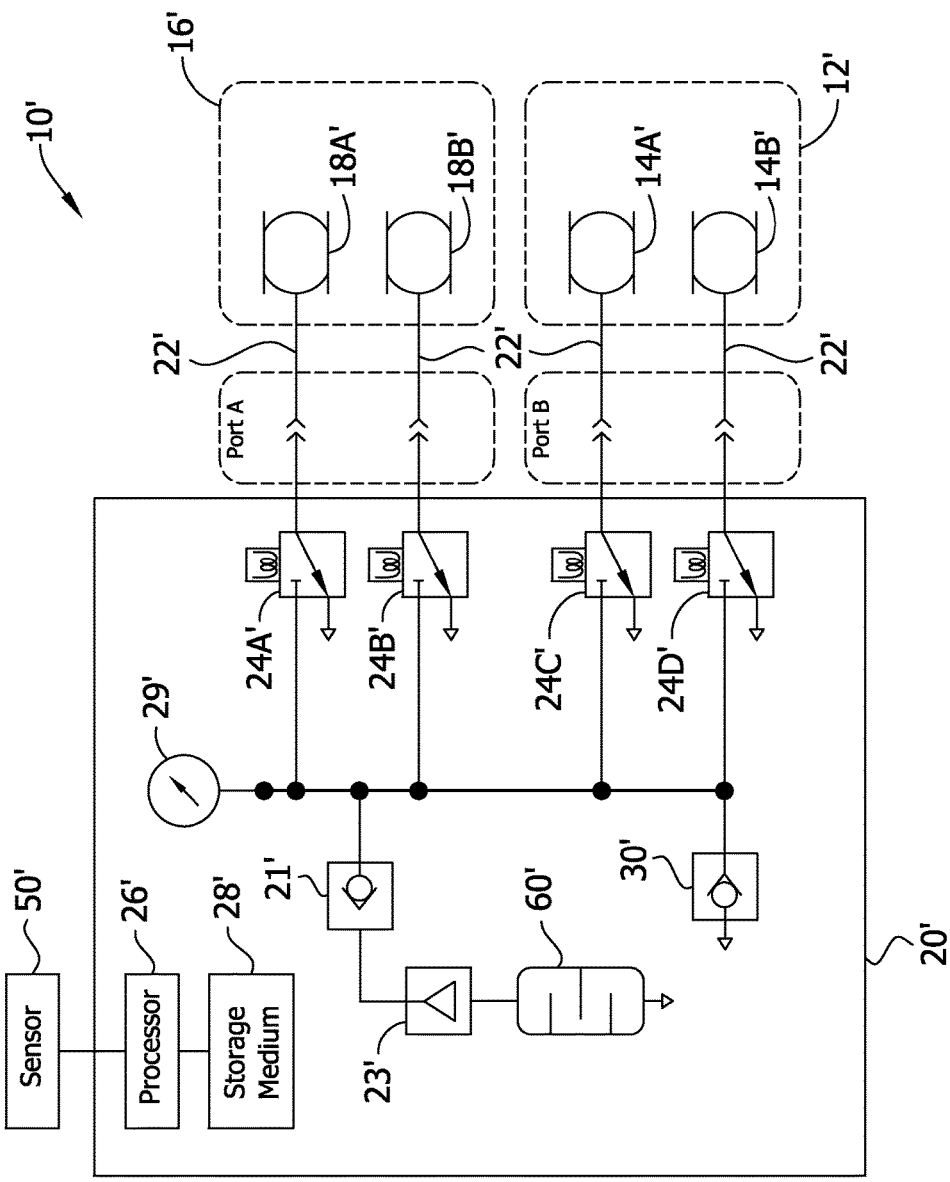
FIG. 5 is a diagram of a pneumatic circuit of the compression system of FIG. 4.

Referring to FIG. 5-6A, an exemplary computer-implemented method of operation of the compression system 10' is described. As described in further detail below, the method includes directing pressurized fluid to inflate the inflatable bladders 14A', 14B', 18A', 18B' of the first and second compression garments 12', 16', respectively, while the first and second compression garments 12', 16' are secured to an outer portion of a limb of a subject. As also further described in further detail below, the method further includes, based at least in part on the directed inflation of inflatable bladders 14A',14B', 18A', 18B', controlling forces applied (e.g., through the flow of blood) to an AV fistula in the limb of the subject.

The third valve 24C', the fourth valve 24D', and the pressure relieve valve 30 are closed 200, restricting inflation of the inflatable bladders 14A', 14B' of the first compression garment 12'. The first valve 24A' and second valve 24B' are opened 202, and the bladders 18A', 18B' of the second inflation garment 16' are rapidly inflated 204 (e.g. a rate of about 5 lpm) until the inflatable bladders 18A', 18B' reach a pre-set pressure sufficient to collapse veins proximal to the AV fistula (e.g., about 80 mmHg).

The first and second valves 24A' and 24B' are closed 206 and the source of pressurized fluid 23' can be turned off. The increased pressure restricts blood from leaving the AV fistula which, in turn, allows the AV fistula to fill with blood and dilate due to the capacitive nature of the veins. The veins are allowed to fill for a period of time. In certain embodiments, the period of time is about 5 seconds to about 30 seconds (e.g., about 8 seconds to about 10 seconds).

The pressure relief 30' valve, followed closely by the first valve 24A', are opened 208, allowing a first inflatable bladder 18A' of the second compression garment 16' to vent quickly. In certain embodiments, the first inflatable bladder 18A' vents for about one second. The release of pressure from the first inflatable bladder 18A' can allow blood in the AV fistula to start flowing.

The second valve 24B' is opened 210, deflating the second inflatable bladder 18B' to facilitate the flow of blood freely back toward the subject's heart. A delay in deflating the second inflatable bladder 18B' a period of time after the first inflatable bladder 18A' is deflated provides an initial blood flow through the AV fistula that is at a lower rate, as compared to simultaneous deflation of the first inflatable bladder 18A' and the second inflatable bladder 18B'.

The second valve 24B' and also the first valve 24A' are closed 212. With pressures in the inflatable bladders 18A', 18B' of the arm cuff 16' below 15 mmHg, the pressure relief valve 30' is closed 214.

The inflatable bladders 14A', 14B' of the first compression garment 12' are rapidly pressurized by opening 216 the third valve 24C' and running the source of pressurized fluid 23' for a period of time (e.g., about one second) to inflate the first inflatable bladder 14A'. The fourth valve 24D' is opened 218 to inflate the second bladder 14B' and the source of pressurized fluid 23' is run until a pressure greater than the internal pressure of the AV fistula is achieved (e.g., about 100 mmHg) in both inflatable bladders 14A', 14B'. The staggered opening of the third and fourth valves 24C' and 24D' can facilitate movement of blood from the hand to the wrist and ultimately into the AV fistula. It is believed that this sequence of inflation simulates muscle contraction that may occur in the hand as a result of a subject squeezing a ball. As compared to squeezing a ball, however, this sequence of inflation does not require the subject to have muscle strength sufficient to squeeze a ball. Additionally or alternatively, as compared to squeezing a ball, this sequence of inflation can be more accurately controlled such that the forces on the AV fistula can have a therapeutic effect on the AV fistula (e.g., enhancing the maturation of the AV fistula).

The source of pressurized fluid 23' is shut off 220, and the pressure relief valve 30' is opened 222 along with all of the valves 24A', 24B', 24C', 24D', allowing the remaining air in the system 10' to be released. The timing of the next inflation sequence can occur at a preset rest period of up to about 1 minute.

FIG. 6 is a timing diagram for the inflation and deflation of the inflatable bladders 14A, 14B', 18A', 18B'. The valves 24A', 24B', 24C', 24D' and pressure relief valve 30' are normally open. Therefore, in the diagram, the indication that the valves are open is indicated by the "off" position of the representative line. It should be appreciated, however, that the valves 24A', 24B', 24C', 24D' could be any combination of normally open or normally closed valves without departing from the present disclosure.

While the timing of inflation sequences of the at least one inflatable bladder of the inflation system has been described as occurring at a preset rest period, other strategies for the timing of inflation sequences are additionally or alternatively possible. For example, the timing of inflation sequences of the at least one inflatable bladder can be based on the measurement of one or more physiologic parameters.

For example, referring again to FIG. 5, the compression system 10' may further include a medical sensor 50', such as, for example, a pulse oximeter, to synchronize the compression cycles of the first compression garment 12' and the second compression garment 16' with relevant physiologic parameters, such as pulse rate of the subject. In some embodiments, the medical sensor 50' is a stand-alone device. In certain embodiments, the medical sensor 50' is embedded in the first compression garment 12' (e.g., at either the finger base or wrist). In embodiments in which the medical sensor 50' is a pulse oximeter, the pulse oximeter includes at least one light source-detection pair, such as an LED and photodetector.

Each pulse measured by the medical sensor 50' can serve as a gate to align the timing of inflation of at least one inflatable bladder of the system 10' such that the inflation of the at least one inflatable bladder is in-phase with the natural heart pulsation of the subject. As used in the present disclosure, "in-phase" refers to inflation that occurs in a predetermined pattern in response to the subject's measured pulse by the medical sensor 50'. In certain embodiments, the predetermined inflation pattern occurs at the same time as a pulse of blood is sensed by the sensor 50' such that the inflation augments the natural flow rate of the subject's blood through the AV fistula. In practice, the system 10' may use the sensed signal from the medical sensor 50' to anticipate when a pulse of blood will occur and, based at least in response to this sensed signal, inflate the at least one inflatable bladder of the system 10' at the time of the anticipated pulse. It should be appreciated that, depending on the relative location of the sensor 50' and the at least one inflatable bladder of the system 10', the inflation of the at least one inflatable bladder may occur a period of time after the pulse of the blood is sensed. It is believed that this in-phase inflation can, for example, increase wall shear stress of the AV fistula due to the more rapid flow of blood through the AV fistula, as compared to the subject's natural pulsatile blood flow through the AV fistula. Without wishing to be bound by theory, it is believed that such an increase in wall shear stress can promote the release of nitric oxide (a vasodilator), which promotes vein dilation and proper remodeling of the vein wall (e.g., increased wall thickness while increasing vein lumen diameter). Vein dilation and remodeling of the vein wall can advance the maturation process of the AV fistula for use in hemodialysis treatment.

Additionally or alternatively, each pulse measured by the medical sensor 50' can serve as a gate to align timing of the inflation of the at least one inflatable bladder of the system 10' such that the inflation of the at least one inflatable bladder of the system 10' is out of phase with the natural heart pulsation of the subject. As used in the present disclosure, "out-of-phase" refers to inflation that occurs in a predetermined pattern in response to the subject's pulse, as measured by the medical sensor 50'. For example, out-of-phase inflation can include compression is applied when blood flow is at or near minimal, forcing blood into the AV fistula. In certain embodiments, the out-of-phase inflation occurs a period of time after a pulse of blood is sensed, causing the blood upstream of the at least one inflatable bladder to pool. In practice, the system 10' may use the signal received from the medical sensor 50' to anticipate when a pulse of blood will occur and inflate the at least one inflatable bladder a period of time after the anticipated pulse. It is believed that this out-of-phase inflation can, for example, increase the volume of blood in the AV fistula, resulting in increased hoop stress of the AV fistula. Without wishing to be bound by theory, it is believed that such increased hoop stress of the AV fistula can promote vein dilation and proper remodeling of the vein wall (e.g., increased wall thickness while increasing vein lumen diameter).

Additionally or alternatively, the medical sensor 50' can include an electrocardiograph (EKG) applied to the subject to measure electrical activity of the subject's heart. For example, the EKG can be in electrical communication with the one or more processors 26' such that timing of the inflation of the at least one inflatable bladder of the first inflation garment 12' and the second compression garment 16' can be adjusted to be in-phase or out-of-phase with the natural heart pulsation of the subject in a manner analogous to that described above with respective to the use of the pulse oximeter.

Additionally or alternatively, the pulse rate of the subject can be measured using the second inflation garment 16'. For example, initial inflation of the inflatable bladders 18A', 18B' of the second compression garment 16' can increase the pressure applied on the underlying arteries and veins, which can dynamically increase the compliance of the walls of the underlying arteries and veins. The increased wall compliance can result in an increase in the volumetric magnitude of pulses, which can create minute deflections of one or more of the inflatable bladders 18A', 18B' of the second inflation garment 16'. These small changes in volume can be detected, for example, by a pressure transducer 29' and can be used to determine the underlying pulse rate. The resulting pulse rate measured by the pressure transducer 29' can be used, for example, to time the inflation of the at least one inflatable bladder in the second inflation garment 16' to be in-phase or out-of-phase with the natural heart pulsation of the subject in a manner analogous to that described above with respective to the use of the pulse oximeter.

In each instance in which a sensor (e.g., sensor 50' and/or pressure sensor 29') is used, a physiological parameter signal (e.g., a pulse waveform, pressure signal, etc.) indicative of the subject's pulsatile blood flow through the AV fistula may be produced by the sensor and received by the controller 20'. The one or more processors 26' may direct inflation of at least one of the inflatable bladders 14A', 14B', 18A', 18B' of the first and second compression garments 12', 16' based on the received physiological parameter signal to produce a modified physiological parameter signal indicative of a modified blood flow through the AV fistula. For example, if the physiological parameter signal is a pulsatile flow waveform, inflation of at least one of the inflatable bladders 14A', 14B', 18A', 18B' can cause the medical sensor 50' to record a modified waveform indicative of a modified blood flow through the AV fistula.

In some embodiments, inflation of the inflatable bladders 14A', 14B', 18A', 18B' can cause a shortening of the waves of the pulsatile waveform. This may be indicative of an increase in a blood flow rate through the AV fistula. This "in-phase" modification of the pulsatile blood flow is understood to produce a more rapid flow of blood through the AV fistula which is believed to increase wall shear stress of the AV fistula. Without wishing to be bound by theory, this is believed to cause the release of nitric oxide (a vasodilator), which promotes vein dilation and proper remodeling of the vein wall (e.g., increased wall thickness while increasing vein lumen diameter) which can be beneficial for maturation of the AV fistula.

In some embodiments, inflation of the inflatable bladders 14A', 14B', 18A', 18B' can cause a lengthening of the waves of the pulsatile waveform. This may be indicative of an increase in blood volume at the AV fistula. This "out-of-phase" modification of the pulsatile blood flow is understood to produce a greater volume of blood at the AV fistula which is believed to increase hoop stress of the AV fistula. This is believed to promote vein dilation and proper remodeling of the vein wall (e.g., increased wall thickness while increasing vein lumen diameter) which is beneficial for maturation of the AV fistula.

In certain embodiments, inflation of the inflatable bladders 14A', 14B', 18A', 18B' can cause the pulsatile waveform to change from a pulsed waveform configuration to a more steady-state amplitude configuration. This may be indicative of a change from a pulsatile blood flow to a non-pulsatile blood flow at the AV fistula. Without wishing to be bound by theory, this augmentation of the blood flow is believed to cause a more uniform stress on the venous walls which is believed to be beneficial in the maturation of the fistula.

While the use of both a first compression garment and a second compression garment has been described, it should be appreciated that other arrangements are additionally or alternatively possible. For example, a compression system according to the present disclosure can include only a single compression garment (e.g., a hand pad).

While the second inflation garment and associated inflatable bladder(s) 18, 18' have been described as being located proximal of an AV fistula, it should be appreciated that the second inflation garment can be positionable over the AV fistula. In this position, the second compression garment (e.g., second compression garment 16, 16') can be operated to apply a relatively constant pressure for a predetermined period of time (e.g., 5 minutes). Without wishing to be bound by theory, it is believed this direct compression the AV fistula releases nitric oxide (a vasodilator), which promotes vein dilation and proper remodeling of the vein wall (e.g., increased wall thickness while increasing vein lumen diameter).

While the first compression garment, and associated inflatable bladder(s), have been described as being distal of the AV fistula and the second compression garment, and associated inflatable bladder(s), have been described as being located proximal of the AV fistula, it should be appreciated that the compression garments can be positionable in other locations relative to the AV fistula. Additionally or alternatively, a location of the compression garments can change based on the stage of the maturation process of the AV fistula.

While the first compression garment, and associated inflatable bladder(s), have been described as being operable to modify blood flow through an AV fistula to promote maturation of the AV fistula, it should be appreciated that inflation of the bladder(s) of the first inflation garment can modify blood flow through an AV fistula to remove thrombogenic material from the AV fistula. Inflating a bladder disposed distally of the AV fistula forces blood through the fistula to impinge upon the thrombogenic material in the fistula and dislodge the material from the fistula. For example, the bladder(s) 14, 14' of the hand pad 12, 12' can be inflated to remove thrombogenic material from the AV fistula.

While the medical sensor 50' has been described as sensing a pulsatile blood flow for producing a waveform indicative of the blood flow through an AV fistula, it should be appreciated that the sensor may additionally or alternatively detect thrombogenic material in the AV fistula. For instance, an abnormality in a signal of the medical sensor 50' may indicate that thrombogenic material is present in the AV fistula. Additionally or alternatively, other sensors such as an ultrasound sensor may detect the presence of thrombogenic material. Additionally or alternatively, a pressure difference between bladders in two compression garments of the system may indicate that thrombogenic material is present in the AV fistula.

While the use of tubing has been described for the connection of a controller to one or more compression garments, it should be appreciated that other arrangements are additionally possible. For example, a controller can be mounted directly to the one or more compression garments, which can eliminate the need for tubing.

While the source of pressurized fluid has been described as including, for example, a pump, other configurations are additionally or alternatively possible. For example, a noise reducing muffler 60, 60' (FIGS. 2 and 5) and/or an accumulator (not shown) can be used to facilitate rapid pressurization of the inflatable bladders.

Embodiments can be implemented in electronic circuitry, or in computer hardware, firmware, software, or in combinations thereof. The controller of the compression system can be implemented in a computer program product tangibly embodied or stored in a machine-readable storage device for execution by a programmable processor; and method actions can be performed by a programmable processor executing a program of instructions to perform functions of the controller of the compression system by operating on input data and generating output. The controller of the compression system can be implemented in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language.

Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD ROM disks. Any of the foregoing can be supplemented by, or incorporated in, ASICs (application-specific integrated circuits).

A number of embodiments have been described. Nevertheless, it will be understood that various modifications may be made without departing from the spirit and scope of the disclosure. Accordingly, other embodiments are within the scope of the following claims.

What is claimed is:

1. A method comprising:
    directing pressurized fluid using a controller comprising a source of pressurized fluid to inflate at least one inflatable bladder of a first compression garment secured to an outer portion of a limb of a subject and at least one inflatable bladder of a second compression garment secured to an outer portion of a limb of a subject
    wherein the controller is in fluid communication with the first and second compression garments through tubing sets; and
    based at least in part on the directed inflation of the at least one inflatable bladder of the first compression garment and the at least one inflatable bladder of the second compression garment, controlling forces applied to an arteriovenous fistula in the limb of the subject;
    receiving at least one physiological parameter signal representative of one or more physiological parameters of the subject, wherein directing pressurized fluid is based at least in part on the at least one received physiological parameter signal to accomplish at least one of increasing the flow rate of blood through the arteriovenous fistula above a pulsatile flow rate and increasing the volume of blood in the arteriovenous fistula above a pulsatile volume of blood in the arteriovenous fistula to advance maturation of the fistula.

2. The method of claim 1, wherein the at least one physiological parameter signal is indicative of natural pulsatile blood flow through the arteriovenous fistula.

3. The method of claim 2, wherein directing pressurized fluid based at least in part on the physiological parameter signals indicative of natural pulsatile blood flow through the arteriovenous fistula includes inflating the at least one inflatable bladder to alter the physiological parameter signal from a natural pulsatile flow signal to a modified flow signal.

4. The method of claim 2, wherein directing pressurized fluid to inflate the at least one inflatable bladder of the first compression garment and the at least one inflatable bladder of the second compression garment includes cyclically inflating and deflating the at least one inflatable bladder of the first compression garment and the at least one inflatable bladder of the second compression garment, with initiation each inflation and deflation cycle of the at least one inflatable bladder of the first compression garment and the at least one inflatable bladder of the second compression garment based at least in part on the signal indicative of the natural pulsatile blood flow through the arteriovenous fistula.

5. The method of claim 4, wherein directing pressurized fluid to cyclically inflate and deflate the at least one inflatable bladder of the first compression garment and the least one inflatable bladder of the second compression garment based at least in part on the signal indicative of natural pulsatile blood flow through the arteriovenous fistula includes inflating the at least one inflatable bladder of the first compression garment and the at least one inflatable bladder of the second compression garment to alter the natural pulsatile blood flow signal to a modified flow signal.

6. The method of claim 2, further comprising determining a waveform of blood flow through the arteriovenous fistula based at least in part upon the signal indicative of natural pulsatile blood flow through the arteriovenous fistula, wherein directing pressurized fluid to inflate the at least one inflatable bladder of the first compression garment and the at least one inflatable bladder of the second compression garment further includes inflating the at least one inflatable bladder of the first compression garment and the at least one inflatable bladder of the second compression garment based at least in part on the determined waveform.

7. The method of claim 2, wherein the received signal indicative of natural pulsatile blood flow through the arteriovenous fistula is at least one of a measure of blood pulsation of the subject received from a pulse oximeter arranged at the at least one inflatable bladder of the first or second compression garment, a measure of electrical activity of the subject's heart received from an electrocardiogram connected to the subject, and a measure of pressure received from the pressure sensor in fluid communication with the at least one inflatable bladder of the first compression garment and the at least one inflatable bladder of the second compression garment.

8. The method of claim 1, wherein the controlled forces applied to the arteriovenous fistula impart a therapeutic effect on the arteriovenous fistula.

9. The method of claim 8, further comprising receiving a sensor signal indicative of thrombogenic material in the vicinity of the arteriovenous fistula, wherein controlling inflation of the at least one inflatable bladder of the first compression garment and the at least one inflatable bladder of the second compression garment includes inflating the at least one inflatable bladder of the first compression garment and the at least one inflatable bladder of the second compression garment based at least in part on the received sensor signal indicative of thrombogenic material.

10. The method of claim 9, wherein the received sensor signal is an ultrasound sensor signal.

11. The method of claim 1, wherein directing pressurized fluid to inflate the at least one inflatable bladder of the first compression garment and the at least one inflatable bladder of the second compression garment includes inflating a first inflatable bladder of the second compression garment disposed on the limb proximal to the arteriovenous fistula to compress an outer portion of the limb proximal to the arteriovenous fistula, and inflating a first inflatable bladder of the first compression garment disposed on the limb distal to the arteriovenous fistula to compress an outer portion of the limb distal to the arteriovenous fistula a period of time after the first inflatable bladder of the second compression garment is inflated.

12. The method of claim 11, wherein inflating the first inflatable bladder of the first compression garment and first inflatable bladder of the second compression garment includes inflating the first inflatable bladder of the first compression garment after the first inflatable bladder of the second compression garment has been deflated.

13. The method of claim 1, wherein the first compression garment is placed on the limb distal to the arteriovenous fistula.

14. The method of claim 13, wherein the first compression garment is placed on a hand of the subject.

15. The method of claim 1, wherein the second compression garment is placed on the limb proximal to the arteriovenous fistula.

16. The method of claim 15, wherein the second compression garment is placed on an upper arm of the subject.

* * * * *